United States Patent [19]

Forfitt et al.

[11] Patent Number: 5,772,596
[45] Date of Patent: Jun. 30, 1998

[54] OSTEOPOROSIS APPARATUS

[75] Inventors: Roy Forfitt, Whiteparish; Ian Alistair Ritchie, Broughton, both of United Kingdom

[73] Assignee: Selkirk Technologies, Inc., Quebec, Canada

[21] Appl. No.: 776,355

[22] PCT Filed: Jul. 24, 1995

[86] PCT No.: PCT/GB95/01747

§ 371 Date: Jan. 24, 1997

§ 102(e) Date: Jan. 24, 1997

[87] PCT Pub. No.: WO96/03080

PCT Pub. Date: Feb. 8, 1996

[30] Foreign Application Priority Data

Jul. 25, 1994 [GB] United Kingdom .................. 9414909

[51] Int. Cl.⁶ ..................................................... A61B 8/00
[52] U.S. Cl. .......................................... 600/449; 600/459
[58] Field of Search ....................... 128/660.01, 660.02, 128/660.06, 661.03, 660.09, 663.01; 73/597, 599, 644; 600/437–438, 442, 449, 445, 472

[56] References Cited

U.S. PATENT DOCUMENTS

| | | | |
|---|---|---|---|
| 4,059,098 | 11/1977 | Murdock | 128/663.01 |
| 5,014,970 | 5/1991 | Osipov | 269/328 |
| 5,134,999 | 8/1992 | Osipov | 128/661.03 |
| 5,335,661 | 8/1994 | Koblonski | 128/661.03 |

*Primary Examiner*—Francis Jaworski
*Attorney, Agent, or Firm*—Ware, Fressola, Van Der Sluys & Adolphson LLP

[57] ABSTRACT

Osterporosis apparatus for measuring ultrasonic characteristic(s) of a patient's bone includes two ultrasonic transducers spacedly arranged in a respective head in the apparatus for ultrasonic transmission from one to the other; circuitry for controlling transmission from the one transducer, measuring the reception at the other and providing an output indicative of the ultrasonic characteristic(s), the apparatus including a fluid system having two diaphragms arranged in the respective heads so that there is a fluid path from each transducer to its diaphragm and a gap between the diaphragms which is occupied in use by the patient's bone.

16 Claims, 4 Drawing Sheets

OSTEOPOROSIS APPARATUS

THE FIELD OF THE INVENTION

The present invention relates to apparatus for the detection and measurement of osteoporosis.

BACKGROUND OF THE INVENTION

It is known that detection of the attenuation and transmissibility of ultrasound through bone is a useful measure of osteoporosis. Conveniently the measurement is made on the heel bone, as a large bone surrounded by little flesh.

Two main types of apparatus are used. In one, a foot bath is used. It has a pair of transducers fixedly arranged in opposite sidewalls of the bath. One transducer is for transmission and the other is a receiver. The bath is filled with water. This apparatus produces repeatable results, but suffers from poor portability and a relatively long time—of the order of 20 minutes—to stabilise before use, whilst the water is de-gassed and heated to blood temperature.

In the second type of apparatus, the transducers are movable towards and away from each other, by means of a mechanism able to relay their separation to detection circuitry. The transducers directly abut the patient's skin at the heel. This apparatus is more readily portable, but has leas good reproduceability.

THE INVENTION

The object of the present invention is to provide apparatus having the repeatability of the water bath apparatus and the portability of the dry apparatus.

According to the invention there is provided osteoporosis apparatus for measuring ultrasonic characteristic(s) of a patient's bone, the apparatus comprising:

two ultrasonic transducers spacedly arranged in respective heads in the apparatus for ultrasonic transmission from one to the other;

circuitry for controlling transmission from the one transducer, measuring the reception at the other and providing an output indicative of the ultrasonic characteristic(s); the apparatus including:

a fluid system having two diaphragms arranged in the respective heads so that there is a fluid path from each transducer to its diaphragm and a gap between the diaphragms which is occupied in use by a patient's bone.

It is envisageable that the spacing of the transducers in the apparatus is adjustable to provide a standard length of fluid path. However, in the preferred embodiment, the spacing of the transducers in the apparatus is fixed and the diaphragms are adjustable to accommodate differing thicknesses of patients' bones, since the transmission of ultrasound through water occurs with little attenuation and a predictable velocity which can be allowed for.

Preferably the fluid system is adapted to be pressurised for adjustment of the diaphragms by inflation against the patient. The diaphragms can be mounted on annular supports, with outer annular sleeves provided around the supports for limiting radial inflation of the diaphragms. Conveniently, the diaphragms are carried on respective tubes—including the annular supports—the tubes being able to be advanced for adjustment of the apparatus to suit patients having differing bone thicknesses.

In one alternative, the tubes are threaded and adapted for diaphragm advance by screw action. Alternatively, the tubes are resilient for extension under fluid pressure for diaphragm advance. In this case, the tubes can have concertina formations for their resilient extension.

It is envisaged that the fluid system may be divided into separate portions, one for each transducer. However, the fluid system preferably includes, a fluid interconnection between the fluid paths to each transducer for diaphragm pressure equalisation, with the interconnection being arranged to avoid ultrasound transmission along it.

The fluid system may be open, with diaphragms' flexibility under the system's own hydraulic head biasing them into contact with the patient. However, again it is preferred that it is closed or closable and provided with means for pressurisation, whereby the diaphragms can be urged into contact with the patient. The arrangement provides that there is little in the ultrasound path between the transducers other than water and the patient's heal bone, with the diaphragms being in good air excluding contact with the patient's skin. Conveniently, the pressurisation means is an air pump arranged to pump air into a region of the fluid system higher than the transducers and the diaphragms.

Preferably, the apparatus includes a sensor for sensing the temperature of the fluid and the circuitry is adapted to compensate the measurements for the temperature.

Conveniently the fluid used in the system is water, but of a quantity able to reach operating conditions in a short period of the order of one minute. Alternatively other liquids such as a castor oil may be used.

Whilst two transducers are preferred, it is conceivable that an array of more than two may be used.

THE DRAWINGS

To help understanding of the invention, a specific embodiment thereof will now be described by way of example and with reference to the accompanying drawings, in which.

PREFERRED EMBODIMENT

Figure 1:
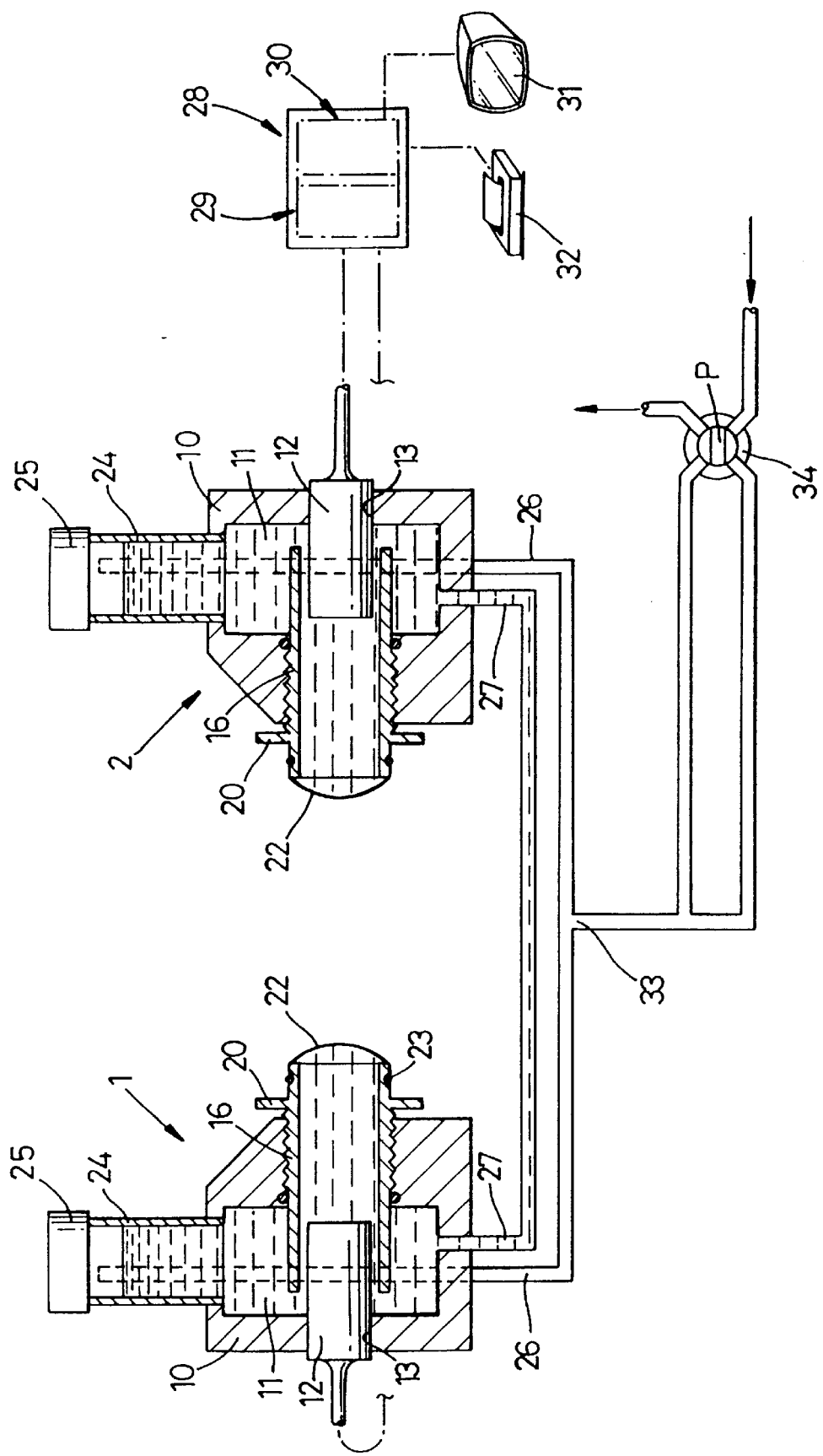
FIG. 1 is a diagrammatic view of osteoporosis apparatus of the invention.

The apparatus shown in the drawings has two essentially identical heads 1,2, one only of which will first be described in detail with particular reference to FIG. 1. Each head has a body 10 defining a central reservoir 11. To one side of the reservoir, an ultrasonic transducer 12 is fluid tightly fixed in a bore 13 in the body. Opposite the transducer, the body has a threaded bore 14 with an O-ring groove 15 adjacent the reservoir. A tubular member 16 is threaded in the bore 14. It has a plain inner section 17 on which an O-ring 18 in the groove 15 acts to prevent escape of fluid along the bore 14. The outer end 19 of the tube has a knurled adjusting wheel 20 and an external groove 21 at the terminal end of the tube. An elastomeric material diaphragm 22 with a bead 23 is fluid tightly stretched across the mouth of the tube with its bead engaged in the groove 21.

An upper extension 24 of the body forms an upper reservoir and is sealed by a cap 25. A pressurisation tube 26 extends from the top of the extension. Also an interconnection tube 27 extends from the bottom of the reservoir.

Referring now to FIG. 1, the pressurisation tubes 26 of the two heads 1,2 are connected together as are the interconnection tubes. The two transducers are connected to a control unit 28. The unit includes circuitry 29 for controlling transmission from the one transducer, further circuitry 30 for measuring the reception at the other transducer. A display 31 and a printer 32 are provided for showing an output indicative of the ultrasonic characteristic(s). The pressurisation tubes are connected via a Tee piece 33 to a three position valve 34. In one position P, that shown in FIG. 1, the tubes 26 are isolated from the ambient for transport of the apparatus. In a second position, for set up, the tubes are connected to the ambient atmosphere. In the third position, the tubes are connected to low pressure gas, typically nitrogen at 0.06 bar (1 psig), for use of the apparatus to make a measurement. At all times the reservoirs are connected by the interconnection tubes 27. The heads are held at a fixed distance apart by a frame 35, shown diagrammatically as a heel support.

Figure 2:
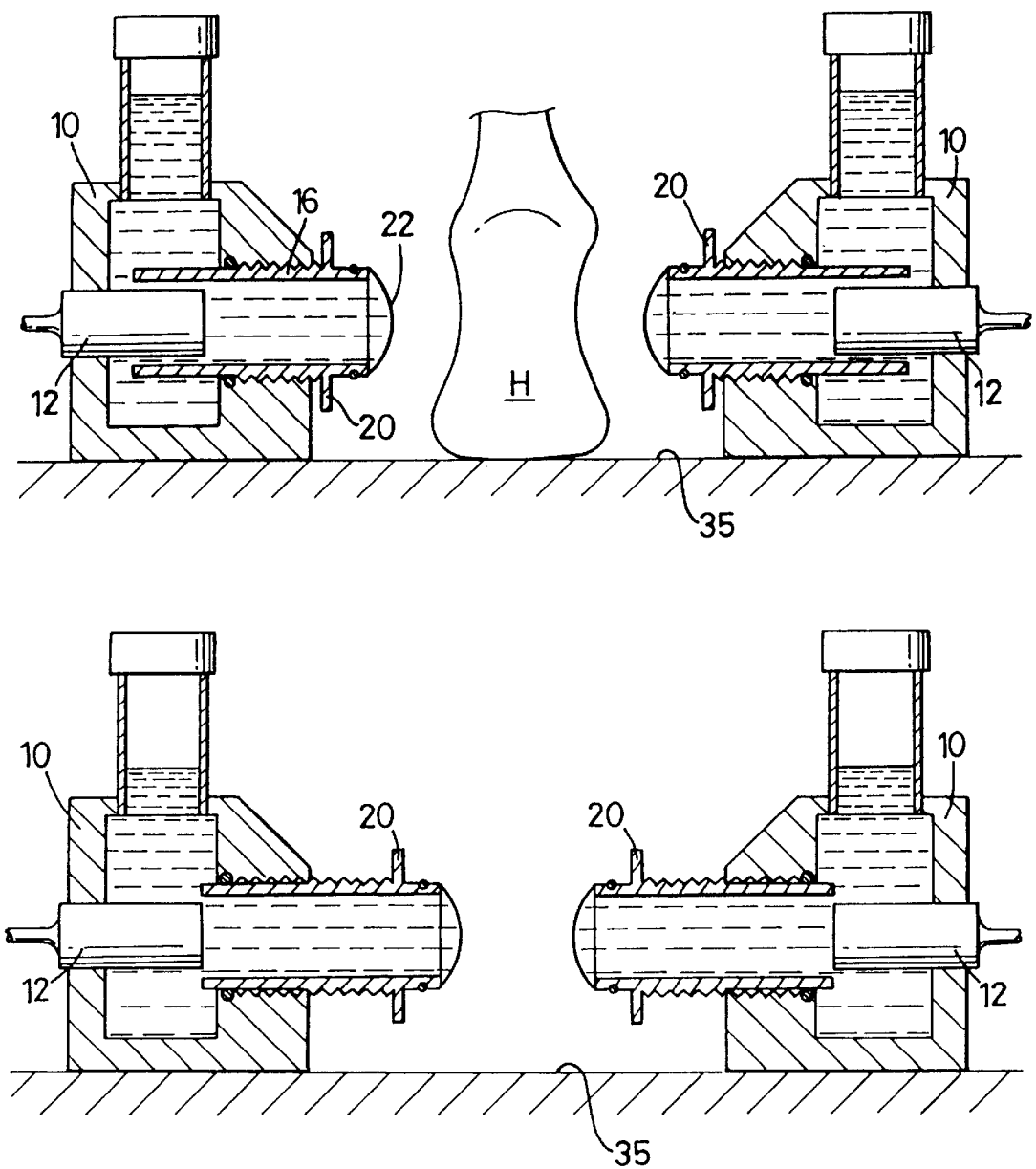
FIG. 2 is a similar view of measurement heads of the apparatus of FIG. 1 in fully retracted and fully extended positions.
Figure 3:
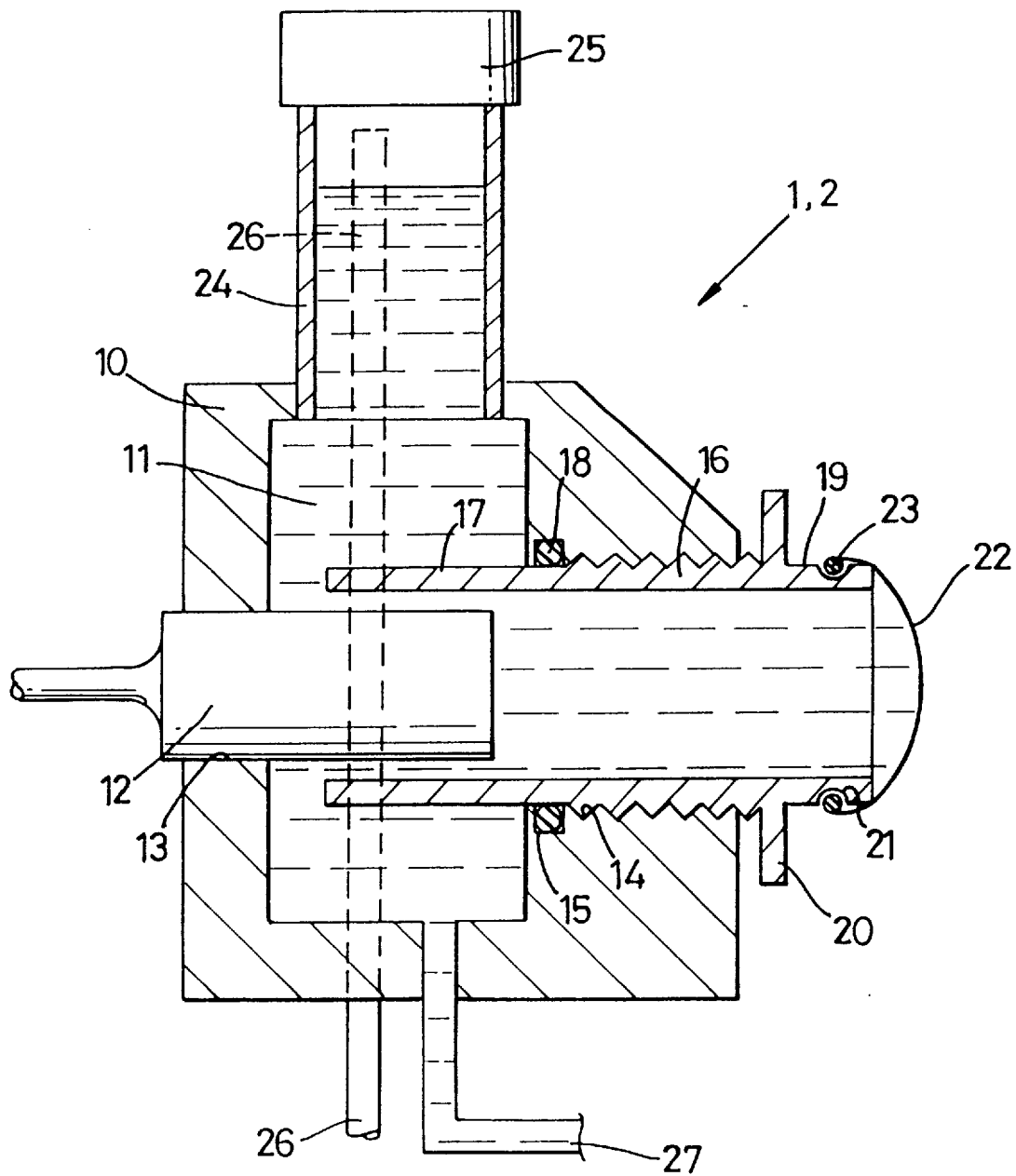
FIG. 3 is view on a large scale of one measurement head.

In use, the reservoirs are filled with water or other fluid having a high transmissibility to ultrasound. The fluid finds its own level via the interconnection tube so that the levels in the two reservoirs are the same. It should be noted that since the interconnection tubes extend from the reservoirs remote from the active front faces of the transducers, they do not provide a ready path for ultrasound between the heads. Referring to FIG. 2, the diaphragm tubes 16 are screwed in or out to bring the diaphragms 22 into contact with the heel H of a patient supported on the frame 35, the upper position in FIG. 3 being for a thick heel and the lower for a thin heel. To ensure good ultrasound transmission, an acoustic gel is applied between the diaphragms and the heel. With the diaphragms in contact with the heel via the gel, the valve 34 is turned to its third—pressure—position. The applied pressure stretches the diaphragms 22 into firm contact with the heel excluding air from between them the the patients skin. The control unit then operates the transducers as transmitter and receiver to measure the transmissibility and attenuation property to ultrasound of the heel, that is to say of its bone, which occupies the majority of the space between the diaphragms.

After measurement, the valve 34 is adjusted to correct the tubes 26 to ambient, removing pressure from the diaphragms 22. The knurled wheels 20 may be used to withdraw the tubes 16 from the heel, allowing the patient's foot to be withdrawn.

Second Embodiment

Figure 4:
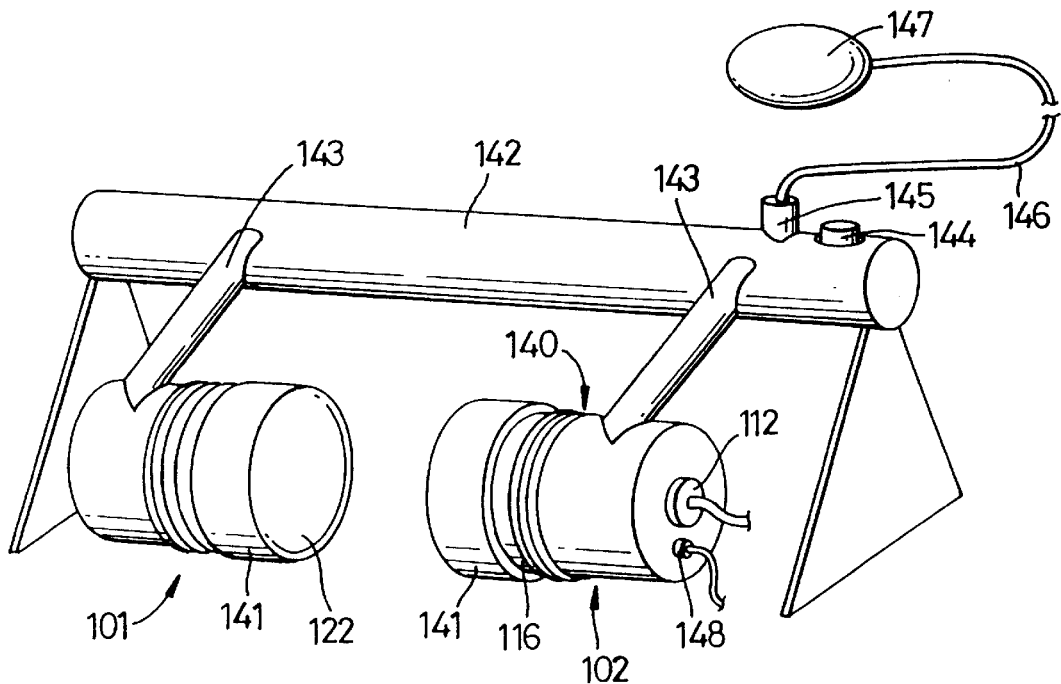
FIG. 4 is a diagrammatic perspective view of a second osteoporosis apparatus according to the invention and FIG. 5 is a cross-sectional side view of one of the heads of the second apparatus.
Figure 5:
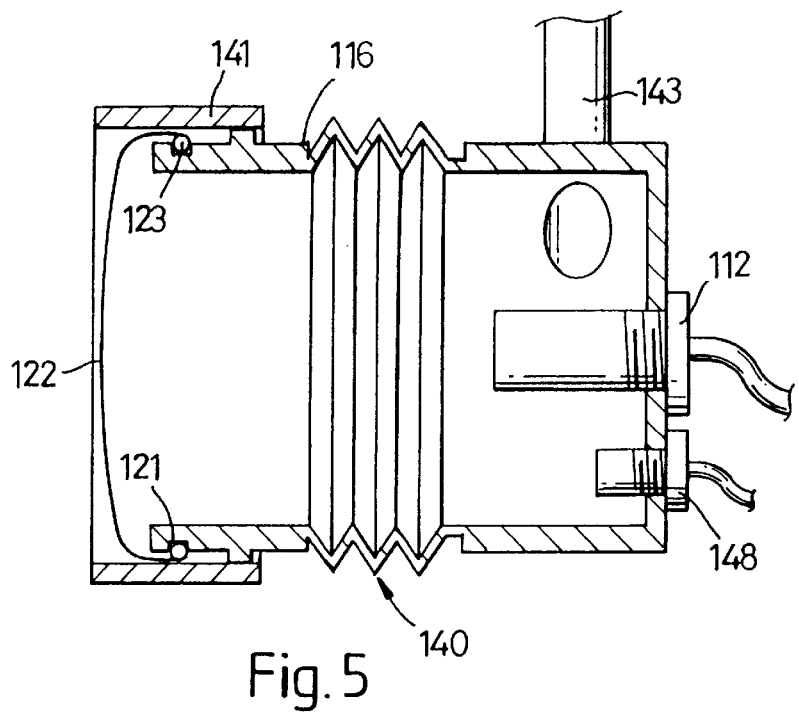

Referring now to FIGS. 4 and 5, the apparatus thereshown has heads 101,102, which are similar to the heads 1,2 with transducers 112, except that their tubes 116 are of flexible material, with a concertina circumferential ridges 140. These allow the tubes to extend under applied pressure. The ends of the tubes carry diaphragms 122 with beads 123 engaged in grooves 121. Surrounding the latter are short sleeves 141, which each extend a short distance beyond the free surface of its diaphragm when un-pressurised. The heads are interconnected by a reservoir tube 142 above and connected to them by branches 143 that extend down from the reservoir 142. This arrangement provides that any air in the heads rises into the reservoir, which as a filler cap 144 and a connection 145 for a flexible tube 146 leading to a bulb-type, manual inflator 147.

In use, the patient's heel is positioned between the heads 101,102 and the reservoir is pressurised. The diaphragms are extended towards the heel, both by their own stretching and concertina extension of the tubes 116. Radial stretching of the diaphragms is inhibited by the sleeves 141. The bulb is pumped until the diaphragms are in firm contact with the heel. Then measurements are taken. The air pumped in is allowed to escape at the bulb for release of the heel, the connection 145 being at a high point on the reservoir. Thus the air in it collects at the connector 145.

A temperature sensor 148, typically a thermistor, is provided for measuring the temperature of the water. This allows an adjustment for temperature dependent speed of sound in the water to be made to the measurements of ultrasonic characteristics of the heel. For this adjustment, the length of the water path between the transducers, of the order of 75 mm, can be assumed to be constant. The heel is assumed to have a nominal thickness of 40 mm. Alternatively its thickness can be measured and the ultrasonic measurements interpreted accordingly.

Variant of the Second Embodiment

In a non-illustrated variant, the reservoir tube is divided in two, with the two parts being mounted for movement towards each other. With this arrangement, the two diaphragms can be can be advanced close to the heel be fore pressurisation; and then pressurised for contact with the heel. Since the two heads are hydraulically separate, each diaphragm must be separately pressurised. This can be effected by connection to individual manometer tubes, to which water is added to provide a determined head for each diaphragm.

Further it is envisaged that each diaphragm and concertina bellows may be a single moulding of resilient plastics material. It can be connected to its head by a peripheral bead engaging in a circumferential groove in the head in the manner of the diaphragms 22,122.

We claim:

1. An osteoporosis apparatus for measuring ultrasonic characteristic(s) of a patient's bone, the apparatus comprising:

two ultrasonic transducers spacedly positioned in respective heads in the apparatus for ultrasonic transmission from one to the other;

circuitry for controlling transmission from the one transducer, measuring the reception at the other and providing an output indicative of the ultrasonic characteristics(s); the apparatus including:

two diaphragms positioned in the respective heads;

structural spacing means that permits the diaphragms to be brought in contact with the patient's bone so that there is a fluid path from each transducer to its diaphragm and a gap between the diaphragms which is occupied in use by the patient's bone, wherein the diaphragms are connected by a fluid system which is adapted to be pressurised for adjustment of the diaphragms by inflation against the patient's bone.

2. An osteoporosis apparatus as claimed in claim 1, having means for adjustable spacing the transducers in the apparatus so as to provide a standard length of fluid path.

3. An osteoporosis apparatus as claimed in claim 1, having means for fixedly spacing the transducers in the apparatus and further having means for adjusting the diaphragms relative to each other so as to accommodate differing thicknesses of the patient's bone.

4. An osteoporosis apparatus as claimed in claim 3, wherein the diaphragms are mounted on annular supports and outer annular sleeves are provided around the supports for limiting radial inflation of the diaphragms.

5. An osteoporosis apparatus as claimed in claim 4, wherein the diaphragms and annular supports are carried on respective tubes, the tubes having advancement means for adjustment of the apparatus to suit patients having differing bone thicknesses.

6. An osteoporosis apparatus as claimed in claim 5, wherein the tubes are threaded and adapted for diaphragm advance by screw action.

7. An osteoporosis apparatus as claimed in claim 5, wherein the tubes are resilient for extension under fluid pressure for diaphragm advance.

8. An osteoporosis apparatus as claimed in claim 7, wherein the tubes have concertina formations for their resilient extension.

9. An osteoporosis apparatus as claimed in claim 8, wherein each diaphragm and respective concertina formations is formed as a single moulding of resilient plastics material and includes a peripheral bead engaging in a circumferential groove in the respective head for securing of the diaphragm to the head.

10. An osteoporosis apparatus as claimed in claim 9, wherein the fluid system includes a fluid interconnection between the fluid paths to each transducer for diaphragm pressure equalisation, said apparatus having means for arranging the fluid interconnection so as to avoid ultrasound transmission along the fluid interconnection.

11. An osteoporosis apparatus as claimed in claim 1, wherein the fluid system is divided into separate portions, one for each transducer.

12. An osteoporosis apparatus as claimed in claim 1, wherein the fluid system is open, wherein the diaphragms are flexible and wherein the apparatus includes hydraulic head biasing means for biasing the diaphragms into contact with the patient's bone.

13. An osteoporosis apparatus as claimed in claim 1, wherein the fluid system is closed or closable and provided with means for pressurisation, whereby the diaphragms can be urged into contact with the patient.

14. An osteoporosis apparatus as claimed in claim 13, wherein the pressurisation means is an air pump arranged to pump air into a region of the fluid system higher than the transducers and the diaphragms.

15. An osteoporosis apparatus as claimed in claim 1, including a sensor for sensing the temperature of the fluid and the circuitry is adapted to compensate the measurements for the temperature.

16. An osteoporosis apparatus as claimed in claim 1, wherein the fluid is water.

* * * * *

UNITED STATES PATENT AND TRADEMARK OFFICE
CERTIFICATE OF CORRECTION

PATENT NO. : 5,772,596
DATED : June 30, 1998
INVENTOR(S) : Roy Forfitt
　　　　　　　Ian Alistair Ritchie It is certified that error appears in the above-identified patent and that said Letters Patent is hereby corrected as shown below:

Column 1, line 25, "leas" should be --less--.
Column 2, line 5, after "includes", delete ",".
Column 4, line 54 (Claim 2, line 2), "adjustable" should be --adjustably--.

Signed and Sealed this

Second Day of March, 1999

*Attest:*

Q. TODD DICKINSON

*Attesting Officer*　　*Acting Commissioner of Patents and Trademarks*